United States Patent [19]

Simons

[11] 4,396,726

[45] Aug. 2, 1983

[54] PROCESS FOR PREPARING ETHYLENE GLYCOL AND LOWER MONOHYDRIC ALCOHOLS FROM SYN GAS USING A NOVEL CATALYST SYSTEM

[75] Inventor: Leslie H. Simons, Austin, Tex.

[73] Assignee: Texaco Inc., White Plains, N.Y.

[21] Appl. No.: 339,237

[22] Filed: Jan. 13, 1982

[51] Int. Cl.³ .................. C07C 27/06; C07C 29/15
[52] U.S. Cl. ................................ 518/700; 518/715
[58] Field of Search ............................ 518/700, 715

[56] References Cited

U.S. PATENT DOCUMENTS 4,332,914 6/1982 Knifton ........................ 518/200

*Primary Examiner*—Howard T. Mars

*Attorney, Agent, or Firm*—Carl G. Ries; Jack H. Park; Walter D. Hunter

[57] ABSTRACT

Ethylene glycol and lower monohydric alcohols are prepared from syn gas in improved yields by contacting a mixture of carbon monoxide and hydrogen with a catalyst system comprising a ruthenium-containing compound and a special manganese-containing compound, both dispersed in a low melting quaternary phosphonium compound, and heating the resulting reaction mixture at a temperature of at least 150° C. and a pressure of at least 500 psi for sufficient time to produce the desired ethylene glycol and monohydric alcohols, and then recovering the same from the reaction mixture.

20 Claims, No Drawings

PROCESS FOR PREPARING ETHYLENE GLYCOL AND LOWER MONOHYDRIC ALCOHOLS FROM SYN GAS USING A NOVEL CATALYST SYSTEM

BACKGROUND OF THE INVENTION

1. Field of the Invention

This invention relates to a new process for preparing ethylene glycol and lower monohydric alcohols. More particularly, the invention relates to an improved process for preparing ethylene glycol and lower monohydric alcohols from syn gas using a novel catalyst system.

Specifically, the invention provides a new and improved process for preparing ethylene glycol and lower monohydric alcohols from syn gas in improved yields, which process comprises contacting a mixture of carbon monoxide and hydrogen with a catalyst comprising a ruthenium-containing compound and a special manganese-containing compound both dispersed in a low melting quaternary phosphonium salt, and heating the resulting mixture at a temperature of at least 150° C. and a pressure of at least 500 psi for sufficient time to produce the desired glycol and monohydric alcohols.

2. Prior Art

Ethylene glycol is a chemical which has found wide use in industry. It is used, for example, in the preparation of plasticizers for vinyl polymers and as a component in polyester fibers and antifreeze formulations. In view of its many uses, there is a need to find new and more economical methods for preparing the ethylene glycol.

One proposed mode of making ethylene glycol involves the reaction of carbon monoxide with hydrogen in the presence of variously proposed catalyst systems. In general, the mixture of carbon monoxide and hydrogen, commonly known as synthesis or syn gas, is reacted at elevated temperatures and pressures in the presence of the proposed catalysts. For example, Belgium Pat. No. 793,086 and U.S. Pat. No. 3,940,432, describe the cosynthesis of ethylene glycol and methanol from mixtures of carbon monoxide and hydrogen using a complex rhodium catalyst. U.S. Pat. No. 3,833,634 describes the use of various other metals as catalysts but indicates that only rhodium and cobalt were effective in producing the ethylene glycol.

However, many of these proposed processes are limited by the nature and activity of the catalyst systems. For example, many of the catalyst systems have poor selectivity, have limited solubility and are expensive to prepare.

It is an object of the invention, therefore, to provide an improved method for preparing ethylene glycol and monohydric alcohols. It is a further object to provide a new process for preparing ethylene glycol and alcohols from syn gas using a new catalyst system. It is a further object to provide a new process for preparing ethylene glycol from syn gas which gives improved yields and greater selectivity. Other objects and advantages of the invention will appear hereinafter.

SUMMARY OF THE INVENTION

It has now been discovered that these and other objects may be accomplished by the process of the invention comprising contacting a mixture of carbon monoxide and hydrogen with a catalyst comprising a ruthenium-containing compound and a special manganese-containing compound both dispersed in a low melting quaternary phosphonium salt, and heating the resulting mixture at a temperature of at least 150° C. and a pressure of at least 500 psi for sufficient time to produce the desired ethylene glycol and monohydric alcohols. It was surprising to find that by the use of these new catalyst system one can obtain greater selectivity in the formation of the ethylene glycol and can obtain the said glycol in higher yields than obtainable heretofore in related synthesis processes from syn gas. Further advantage is found in the fact that the process can be operated at moderate temperatures and pressures and avoids the use of extreme conditions required in many of the prior known processes.

The process of the invention as far as the formation of the desired ethylene glycol is concerned may be represented by the following equation:

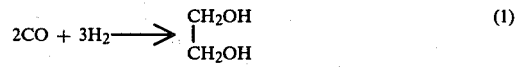

$$2CO + 3H_2 \longrightarrow \begin{array}{l} CH_2OH \\ | \\ CH_2OH \end{array} \quad (1)$$

Typical yields of ethylene glycol based on total liquid products range from 8 to about 20 wt%.

DETAILED DESCRIPTION OF THE INVENTION

In the operation of the process of the invention, ethylene glycol and lower monohydric alcohols, such as methanol and ethanol, are prepared concurrently from a synthesis gas mixture of carbon monoxide and hydrogen by a process comprising the following steps:

(a) Contacting the said mixture of carbon monoxide and hydrogen with a catalyst comprising a ruthenium-containing compound and a special manganese-containing compound, both dispersed in a low melting quaternary phosphonium salt, (b) heating the said mixture to a temperature of at least 150° C. and a pressure of at least 500 psi with sufficient carbon monoxide and hydrogen to satisfy the above-noted stoichiometry of the desired ethylene glycol synthesis, until substantial formation of the desired ethylene glycol has been achieved, and, (c) preferably isolating the said ethylene glycol and monohydric alcohols contained therein.

In order to present the inventive concept of the present invention in the greatest possible detail, the following supplementary disclosure is submitted. The process of the invention is practiced as follows:

As noted, the new catalyst system used in the process of the invention contains a ruthenium-containing compound and a manganese-containing compound. The ruthenium-containing compound to be used may be chosen from a wide variety of organic and inorganic compounds, complexes, etc. It is only necessary that the catalyst component actually employed contain the ruthenium in any of its ionic states.

The ruthenium-containing compound employed may take many different forms. For example, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium nitrate, or as the salt of a suitable organic carboxylic acid, such as, for example, ruthenium(III) acetate, ruthenium naphthenate, ruthenium valerate and ruthenium complexes such as ruthenium(III) acetylacetonate. The ruthenium may also be added to the reaction mixture as a carbonyl or hydrocarbonyl derivative. Suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonyl-ruthenium(II) chloride dimer, $(Ru(CO)_3Cl_2)_2$.

Preferred ruthenium-containing compounds include oxides of ruthenium, ruthenium salts of organic carboxylic acids and ruthenium carbonyl or hydrocarbonyl derivatives. Particularly preferred are the following members: ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The manganese compounds to be used in the catalyst composition comprise those compounds which have one manganese atom attached to carbon, and preferably those organometallic compounds having one manganese atom attached to three separate carbonyl groups and to an unsaturated hydrocarbon radical. Examples of these include, among others, allyl manganese tricarbonyl, cyclohexadienyl manganese tricarbonyl, butadienyl manganese tricarbonyl, cyclohexenyl manganese tricarbonyl, methylcyclopentenyl manganese tricarbonyl, and the like. Preferred manganese compounds include those of the formula

YMn(CO)₃ wherein Y is an unsaturated aliphatic or cycloaliphatic hydrocarbon containing 2 to 16 carbon atoms, such as, for example, allyl manganese tricarbonyl, cyclopentadienyl manganese tricarbonyl, methylcyclopentadienyl manganese tricarbonyl, cyclopentenyl manganese tricarbonyl and hexenyl manganese tricarbonyl.

Particularly preferred manganese compounds to be utilized are those of the formula

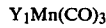

Y₁Mn(CO)₃ wherein $Y_1$ is a cycloalkadienyl radical, such as cyclopentadienyl, cyclohexadienyl, and alkyl or aryl substituted derivatives, such as methylcyclopentadienyl, phenylclopentadienyl, butylcyclohexadienyl and the like.

The ruthenium-containing compound and the manganese-containing compound are preferably first dispersed in a low melting quaternary phosphonium base or salt. The quaternary phosphonium base or salt selected must be relatively low melting, i.e. have a melting point below the temperature of the reaction. Usually quaternary phosphonium compounds employed have a melting point less than about 180° C. and preferably a melting point less than 150° C.

Suitable quaternary phosophonium salts have the formula

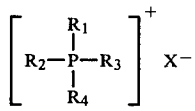

wherein $R_1$, $R_2$, $R_3$ and $R_4$ are organic radicals, particularly aliphatic hydrocarbon radicals, bonded to the phosphorous atom, and X is an anionic species, preferably chlorine or bromide. The preferred organic radicals useful in this instance include those alkyl radicals having 1 to 20 carbon atoms in a branched or linear chain, such as methyl, ethyl, n-butyl, iso-butyl, octyl, 2-ethylhexyl and dodecyl radicals. Tetraethylphosphonium bromide and tetrabutylphosphonium bromide are typical examples presently in commercial production. The corresponding quaternary phosphonium acetates, benzoates, butyrates, and the like, are also satisfactory in this instance.

Illustrative examples of suitable quaternary phosphonium salts include tetrabutylphosphonium bromide, tetraheptylphosphonium bromide, tetrabutylphosphonium acetate, tetrabutylphosphonium benzoate, tetrabutylphosphonium butyrate, octylphosphonium acetate, tetrahexylphosphonium acetate and tetraoctylphosphonium bromide.

The preferred quaternary salts are generally the tetralkylphosphonium salts containing alkyl groups having 1 to 20 carbon atoms, such as methyl, ethyl, butyl, amyl, hexyl and isobutyl. Tetrabutylphosphonium bromides and lower alkanoates are the most preferred.

Generally, in the catalyst system used in the process of the invention, the molar ratio of the ruthenium-containing compound to the quaternary phosphonium salt will range from about 1:0.01 to about 1:100 or more and, preferably, will be from about 1:0.5 to about 1:20.

The quantity of ruthenium-containing compound and the manganese-containing compound to be used in the process of the invention may vary over a wide range. The process is conducted in the presence of a catalytically effective quantity of the active ruthenium-containing compound and the active manganese-containing compound which gives the desired product in a reasonable yield. The reaction proceeds when employing as little as about $1 \times 10^{-6}$ weight percent, and even lesser amounts of the ruthenium-containing compound, together with as little as about $1 \times 10^{-6}$ weight percent of the manganese compound, or even lesser amounts, based on the total weight of the reaction mixture. The upper concentration is dictated by a variety of factors including catalyst cost, partial pressures of carbon monoxide and hydrogen, operating temperature, etc. A ruthenium-containing compound concentration of from about $1 \times 10^{-5}$ to about 10 weight percent in conjunction with a manganese-containing compound concentration of from about $1 \times 10^{-5}$ to about 5 percent, based on the total weight of the reaction mixture is generally desirable in the practice of this invention. The preferred ruthenium to manganese atomic ratios are from 10:1 to 1:10.

Particularly superior results are obtained when the above-noted three components of the catalyst system are combined as follows on a molar basis: ruthenium-containing compound 0.1 to 4 moles, manganese-containing compound 0.1 to 15 moles, and the quaternary phosphonium base or salt 10 to 60 moles and still more preferably when the components are combined in the following ratio: ruthenium-containing compound 1 to 4 moles, manganese-containing compound 1 to 10 moles and the phosphonium base or salt 20 to 50 moles.

The temperature range which can be employed in the process of the invention may vary over a considerable range depending upon experimental factors, including the choice of catalyst, pressure and other variables. A preferred range of operability is from about 150° C. to about 350° C. when superatmospheric pressures of syngas are employed. A narrower range of about 150° C. to 275° C. represents a particularly preferred temperature range.

The pressure employed may also vary over a considerable range, but in most cases is at least above 500 psig. A preferred operating range varies from about 1000 psig to about 7500 psig, although pressures above 7500 psig also provide useful yields of the desired product. The pressures referred to herein represent the total pressure generated by all the reactants, although they are substantially due to the carbon monoxide and hydrogen fractions.

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to about 1:5, although ratios outside these ranges may also be employed with good results. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide and hydrogen present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The desired product of the reaction, ethylene glycol, will be formed in significant quantities generally varying from about 8 wt% to about 20 wt%. Also formed will be significant amounts of the lower monohydric alcohols, such as methanol and ethanol. Other derivatives such as acetic acid and ethylene glycol ethers, may also be formed in very minor amounts. The ethylene glycol, monohydric alcohols and other by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the at, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analyses, or a combination of these techniques. Analyses have, for the most part, been by parts by weight; all temperatures are in degrees centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the improved results obtained by using the new catalyst system comprising the ruthenium-containing compound, manganese-containing compound dispersed in the quaternary phosphonium salt.

Ruthenium dioxide hydrate, $RuO_2.H_2O$, (4 mmole) and methylcyclopentadienyl manganese tricarbonyl, $MeCpMn(CO)_3$, (1 mmole) were dispersed in solid tetrabutylphosphonium bromide (29 mmole) melting at about 100° C., and the mixture transferred in a glass liner to an 850 ml pressure reactor equipped with heating and agitation means. The reactor was sealed, flushed with $H_2/CO$ (1:1). The mixture was heated to 220° C. with rocking, the pressure raised to 5300 psi by $CO/H_2$ addition from a large surge tank, and the reactor held at 220° C. for 5 hours. Pressure was maintained during that period at 5150 to 5300 psi by incremental additions of $CO/H_2$ from the surge tank.

On cooling, a typical gas sample was taken and the excess gas removed. The reddish-brown liquid product (17.2 grams) represented a 6.2 gram gain in weight.

Analysis of the liquid product by GLC showed the presence of:
- 16.1% ethylene glycol
- 36.0% methanol
- 23.2% ethanol
- 2.6% acetic acid
- 4.0% water The ethylene glycol, methanol and ethanol were recovered from the crude liquid product by fractional distillation in vacuo. Distillate fractions typically showed an ethylene glycol content of greater than 10 wt%.

The above results were surprising in view of the results obtained by the use of related catalyst systems in the same process.

For example, the procedure of Example I above was repeated with the exception that the catalyst consisted only of 4 mmole of $RuO_2.H_2O$ and 29 mmole of tetrabutylphosphonium bromide. Temperature was maintained at 220° C. and pressure at 4800 to 4400 psi. At the conclusion of the reaction period of 5 hours, no ethylene glycol was detected in the reaction mixture.

Example I above was also repeated with the exception that the catalyst consisted of 4 mmole of $RuO_2.H_2O$ and 2 mmole of $KMnO_4$ and 29 mmole of tetrabutylphosphonium bromide. The temperature was maintained at 220° C. and the pressure at 5400 psi. At the conclusion of the reaction period of 5 hours, no ethylene glycol was detected in the reaction mixture.

The procedure of Example I above was repeated with the exception that the $RuO_2.H_2O$ and methycyclopentadienyl manganese tricarbonyl was dispersed in 9.5 grams of tetrabutylammonium bromide. The temperature was maintained at 220° C. and the pressure at 4800 psi. After a reaction period of 5 hours, no ethylene glycol was detected in the reaction mixture.

The above results clearly demonstrate the critical nature of the ruthenium-containing compound, manganese-containing compound and the quaternary phosphonium base or salt.

EXAMPLE II

Example I was repeated with the exception that 4 mmole of methylcyclopentadienyl manganese tricarbonyl used with 4 mmole of $RuO_2.H_2O$ and 10 grams of tetrabutylphosphonium bromide. Temperature was maintained at 190° C. and pressure at 4800 psi. Analysis of the reddish-brown liquid product obtained showed the following:
- 20.7% ethylene glycol
- 27.2% methanol
- 10.0% ethanol
- 5.3% water

EXAMPLE III

The procedure of Example I was repeated with the exception that the ratio of the catalyst system was changed as follows: 4 mmole of methylcyclopentadienyl manganese tricarbonyl, 4 mmole of $RuO_2.H_2O$ and 10 grams of the tetrabutylphosphonium bromide. The temperature was maintained at 220° C. and the pressure at 4400 to 5300 psi by incremental addition of the $CO/H_2$ from the surge tank. On cooling, a typical gas sample was taken and the excess gas removed. The reddish-brown liquid product (16.7 grams) represented a 5.0 gram gain in weight.

Analysis of the liquid product by GLC showed the presence of:
- 12.3% ethylene glycol
- 35.8% methanol
- 10.0% ethanol
- 0.9% acetic acid
- 9.4% water

EXAMPLE IV

The procedure of Example I was repeated with the exception that the ratio of the catalyst system was changed as follows: 2 mmole of methylcyclopentadienyl manganese tricarbonyl, 4 mmole of $RuO_2.H_2O$ and 10 grams of tetrabutylphosphonium bromide. The temperature was maintained at 220° C. and pressure of 4200 to 5300 psi. Analysis of the reddish-brown reaction product showed the following:
- 11.3% ethylene glycol
- 40.3% methanol
- 10.2% ethanol
- 1.3% acetic acid
- 13.0% water

EXAMPLE V

The procedure of Example I was repeated with the exception that the catalyst system comprised 2 mmole of the methylcyclopentadienyl manganese tricarbonyl, 4 mmole of $RuO_2.H_2O$ and 10 grams of the tetrabutylphosphonium bromide, and the temperature was maintained at 190° C. Pressure of 4800 to 4900 psi was maintained by incremental addition of the $CO/H_2$ from the surge tank. On cooling, a typical gas sample was taken and the excess gas removed. The reddish brown liquid product gave the following analysis:
- 14.0% ethylene glycol
- 40.9% methanol
- 14.5% ethanol
- 5.3% water

EXAMPLE VI

The procedure of Example I was repeated with the exception that the ratio of the catalyst system was changed as follows: 8 mmole of methylcyclopentadienyl maganese tricarbonyl, 4 mmole of $RuO_2.H_2O$ and 10 grams of tetrabutylphosphonium bromide. The temperature was maintained at 220° C. and pressure at 4800 psi. The resulting reddish-brown liquid product showed the following analysis:
- 12.9% ethylene glycol
- 39.7% methanol
- 12.4% ethanol
- 1.1% acetic acid
- 4.0% water

EXAMPLE VII

Example I is repeated with the exception that the ruthenium oxide is replaced with each of the following: ruthenium(III) acetate, ruthenium(III) acetylacetonate and ruthenium(III) bromide. Related results are obtained.

EXAMPLE VIII

Example I is repeated with the exception that the manganese compound is replaced with each of the following: allyl manganese tricarbonyl, hexenyl manganese tricarbonyl, and cyclohexenyl manganese tricarbonyl. Related results are obtained.

What is claimed is:

1. A process for preparing ethylene glycol and lower monohydric alcohols from syngas which comprises contacting a mixture of carbon monoxide and hydrogen with a catalyst system comprising a ruthenium-containing compound and a manganese-containing compound wherein one manganese atom is attached to three separate carbonyl groups and to an unsaturated hydrocarbon radical, the ruthenium-containing compound and the manganese-containing compound being dispersed in a low melting quaternary phosphonium salt, and heating the resulting mixture at a temperature of at least 150° C. and a pressure of at least 500 psi for sufficient time to produce the desired ethylene glycol and monohydric alcohols.

2. A process as in claim 1 wherein the reaction is conducted at a syngas pressure of about 1000 psi to about 7500 psi.

3. A process as in claim 1 wherein the reaction is conducted at a temperature of from about 150° C. to about 350° C.

4. A process as in claim 1 wherein the ruthenium-containing compound is selected from the group consisting of one or more oxides of ruthenium, ruthenium complexes of carbonyl-containing ligands, ruthenium salts of organic acids and ruthenium-carbonyl and hydrocarbonyl compounds.

5. A process as in claim 1 wherein the ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecarbonyl.

6. A process as in claim 1 wherein the manganese-containing compound is a compound of the formula $YMn(CO)_3$ wherein Y is an unsaturated aliphatic or cycloaliphatic hydrocarbon containing from 2 to 16 carbon atoms.

7. A process as in claim 1 wherein the manganese-containing compound is a cycloalkyladienyl manganese tricarbonyl.

8. A process as in claim 1 wherein the manganese-containing compound is an alkylcycloalkadienyl manganese tricarbonyl wherein the alkyl group contains from 1 to 12 carbon atoms.

9. A process as in claim 1 wherein the ruthenium-containing compound is a ruthenium oxide and the manganese-containing compound is a methylcyclopentadienylmanganese carbonyl.

10. A process as in claim 1 wherein the quaternary phosphonium salt has a melting point less than about 180° C.

11. A process as in claim 1 wherein the quaternary phosphonium salt or base is a tetralkylphosphonium salt.

12. A process as in claim 1 wherein the quaternary phosphonium salt is a tetralkylphosphonium halide wherein the alkyl groups contain from 1 to 6 carbon atoms each.

13. A process as in claim 1 wherein the quaternary phosphonium salt is a tetraalkylphosphonium bromide.

14. A process as in claim 1 wherein the carbon monoxide and hydrogen are utilized in a mole ratio varying from 5:1 to 1:5.

15. A process as in claim 1 wherein the ruthenium-containing compound, manganese-containing compound and the quaternary phosphonium base or salt are utilized in a mole ratio of ruthenium-containing compound 1 to 4 moles, manganese-containing compound 1 to 10 moles and the phosphonium salt or base 20 to 50 moles.

16. A process for preparing ethylene glycol and lower monohydric alcohols from syn gas which comprises contacting a mixture of carbon monoxide and hydrogen in mole ratio of 1:5 to 5:1 with a catalyst system comprising a ruthenium oxide and a manganese compound of the formula $YMn(CO)_3$ wherein Y is an unsaturated aliphatic or cycloaliphatic hydrocarbon, the said ruthenium-containing compound and manganese-containing compound being dispersed in a quaternary phosphonium salt melting below 180° C. and heating the resulting mixture at a temperature between 150° C. and 350° C. and a pressure of 1000 psi to 5500 psi.

17. A process as in claims 1 or 16 wherein the ruthenium-containing compound is ruthenium dioxide hydrate.

18. A process as in claims 1 or 16 wherein the manganese-containing compound is methylcyclopentadienyl manganese tricarbonyl.

19. A process as in claims 1 or 16 wherein the phosphonium salt is tetrabutylphosphonium bromide.

20. A process as in claims 1 or 16 wherein the ruthenium-containing compound is ruthenium(III) acetate.

* * * * *